(12) United States Patent
Grant

(10) Patent No.: US 7,837,846 B2
(45) Date of Patent: Nov. 23, 2010

(54) ELECTROCHEMICAL SENSOR

(75) Inventor: Robert Bruce Grant, Steyning (GB)

(73) Assignee: Edwards Limited, Crawley, West Sussex (GB)

( * ) Notice: Subject to any disclaimer, the term of this patent is extended or adjusted under 35 U.S.C. 154(b) by 1279 days.

(21) Appl. No.: 10/568,331

(22) PCT Filed: Aug. 5, 2004

(86) PCT No.: PCT/GB2004/003370
§ 371 (c)(1),
(2), (4) Date: Feb. 13, 2006

(87) PCT Pub. No.: WO2005/019817
PCT Pub. Date: Mar. 3, 2005

(65) Prior Publication Data
US 2006/0266658 A1 Nov. 30, 2006

(30) Foreign Application Priority Data
Aug. 19, 2003 (GB) ................................. 0319455.2

(51) Int. Cl.
G01N 27/407 (2006.01)
(52) U.S. Cl. ...................................... 204/410; 205/781
(58) Field of Classification Search ................. 204/410, 204/411, 421–429; 205/781, 783.5–785, 205/787
See application file for complete search history.

(56) References Cited
U.S. PATENT DOCUMENTS
4,464,244 A 8/1984 Uchida et al.

(Continued)

FOREIGN PATENT DOCUMENTS
EP 0 949 505 A2 10/1999

OTHER PUBLICATIONS
J. Riegel, H. Neumann, H.-M. Wiedenmann, "Exhaust Gas Sensors for Automotive Emission Control," Solid State Ionics 152-153 (2002) pp. 783-800.

(Continued)

Primary Examiner—Nam X Nguyen
Assistant Examiner—Gurpreet Kaur

(57) ABSTRACT

An organic contaminant molecule sensor is described for use in a low oxygen concentration monitored environment. The sensor comprises an electrochemical cell, which is formed from a measurement electrode coated with (or formed from) a catalyst having the ability to catalyse the dissociative adsorption of the organic contaminant molecule, the electrode being positioned for exposure to the monitored environment, a reference electrode coated with (or comprised from) a catalyst selected for its ability to catalyse the dissociation of oxygen to oxygen anions, the reference electrode being positioned within a reference environment, and a solid state oxygen anion conductor disposed between and bridging the measurement and reference electrodes, wherein oxygen anion conduction occurs at or above a critical temperature, $T_c$. Sealing means are provided for separating the reference environment from the monitored environment. Means are also provided for controlling and monitoring the temperature of the cell, and for controlling the electrical current ($I_p$) flowing between the reference and measurement electrodes. At temperatures ($T_{ads}$) below $T_c$, organic contaminant molecules are adsorbed onto and dissociated at the surface of the measurement electrode leading to the build up of carbonaceous deposits at the surface thereof. At temperatures ($T_{ox}$) above $T_c$, an electrical current ($I_p$) is passed between the reference and measurement electrode thereby to control the number of oxygen anions passing from the reference electrode to the measurement electrode to oxidise the carbonaceous deposits formed at the surface thereof and the formation of carbon dioxide.

36 Claims, 3 Drawing Sheets

U.S. PATENT DOCUMENTS

| | | | |
|---|---|---|---|
| 4,882,030 A | | 11/1989 | Suzuki et al. |
| 5,827,415 A | * | 10/1998 | Gur et al. .................... 204/426 |
| 6,312,585 B1 | | 11/2001 | Wahl et al. |
| 6,355,151 B1 | * | 3/2002 | Brosda et al. ............... 204/424 |
| 2003/0121801 A1 | * | 7/2003 | Inaba et al. .............. 205/785.5 |

OTHER PUBLICATIONS

PCT International Search Report for International Application No. PCT/GB2004/003370; Date of mailing: Nov. 15, 2004.

PCT Written Opinion of the International Search Authority for International Application No. PCT/GB2004/003370; Date of mailing: Nov. 15, 2004.

* cited by examiner

ELECTROCHEMICAL SENSOR

CROSS REFERENCE TO RELATED APPLICATION

This application is a 371 National Stage Application of International Application PCT/GB2004/003370 filed Aug. 5, 2004, which claims priority to a GB Application GB 0319455.2 filed Aug. 19, 2003.

FIELD OF THE INVENTION

This invention relates to a sensor for the detection of organic contaminants in low oxygen concentration process environments, such as those used in the semiconductor manufacturing industry, the use of such sensors and a novel method for the detection of organic contaminants in such process environments. The term "low oxygen concentration process environment" is to be understood to mean a process environment in which the partial pressure of oxygen is of the order of $10^{-6}$ mbar to $10^{-3}$ mbar (parts per billion to parts per million).

BACKGROUND OF THE INVENTION

In, for example, the semiconductor manufacturing industry, it is important to control the atmosphere (the process environment) in which wafers are manufactured. The wafers are desirably manufactured in a controlled environment, as undesirable or varying levels of organic contaminants can result in device and/or equipment failure.

Levels of contaminating organic material in the parts per trillion (ppt) to parts per billion (ppb) range, which corresponds to a partial pressure of $10^{-9}$ mbar to $10^{-6}$ mbar, do not, in general, result in device or equipment failure. However, if the levels of organic contaminants become much higher than this, failures may result. In order to control the process environment, it is necessary to monitor the levels of organic contaminants present. In particular, some processes are sensitive to contaminant material in the low ppb range, and so for these processes it is desirable to monitor the level of contaminant materials in the ppt range. However, such monitoring processes are costly and it is difficult to determine an accurate value for the total organic compounds (TOC) present at such low contaminant levels. In addition, many fabrication processes are tolerant of light saturated hydrocarbons, such as methane ($CH_4$) and ethane ($C_2H_6$), which have particularly low reaction probabilities with most surfaces and therefore do not take part in the various contamination inducing reactions.

In vacuum based process environments, TOC levels are often determined using mass spectrometry, as a mass spectrometer is capable of measuring contamination levels of the order of ppt. However the interpretation of such measurements is often complicated by effects such as mass spectral overlap, molecular fragmentation and background effects, for example.

Although mass spectrometers can be used in process environments operating at ambient pressure or above, additional vacuum and sample handling systems are required, which make such instruments very expensive. Under such conditions, it is preferred to use gas chromatographic techniques to monitor the TOC levels present in the process environment. However, in order to monitor contaminants in the ppt range it is necessary to fit the gas chromatogram with a gas concentrator.

It should be noted that although mass spectrometry and gas chromatography are able to detect ppt levels of TOC, their ability to differentiate the presence of the process-tolerant light hydrocarbons referred to above from the more harmful organic compounds is limited, which makes it difficult to determine the total levels of damaging hydrocarbons in the process environment.

In addition, because the use of either mass spectrometric or gas chromatographic techniques for determining the TOC levels present in process environments requires specialist equipment, they tend to be rather expensive and are typically only used as Point of Entry (POE) monitors for the whole facility rather than the more useful Point of Use (POU) monitors.

Hydrocarbons, including light hydrocarbons such as methane ($CH_4$) and ethane ($C_2H_6$), have been routinely monitored using common tin oxide ($SnO_2$) based sensor devices. These sensors typically operate under atmospheric pressure to detect target gases in the range from tens of ppb (parts per billion) to several thousand ppm (parts per million). This type of sensor works effectively within these ranges by providing a linear output signal that is directly proportional to the quantity of target gas within the monitored environment. Although these sensors are suitable for monitoring contaminant levels within ambient environments, they do not lend themselves for applications with sub-atmospheric processing environments such as those encountered within semiconductor processing environments. Under such vacuum conditions the $SnO_2$-type of sensor will suffer from reduction of the active oxide content leading to signal drift and non-response after a period of time.

Wet potentiometric titration procedures and cyclic voltammetry are frequently used to monitor the levels of known contaminant species in solutions. All of these processes take place in the liquid phase and use reversible electrode processes, mostly using water as the major constituent of the solvent and use electrons to directly effect oxidation/reduction. Gas phase electrochemistry is confined to the areas of electrochemical sensors, both potentiometric and amperometric, and solid oxide fuel cells neither of which use any kind of titration reaction.

It will therefore be appreciated that, in contrast to the wet titrametric procedures of the prior art, the sensor of the present invention facilitates the titrametric determination of trace organic contaminants in the gaseous phase using a solid state electrolyte.

Chemical sensors comprising solid state electrolytes such as oxygen anion conductors, or silver or hydrogen cation conductors, have been used to monitor levels of oxygen, carbon dioxide, and hydrogen/carbon monoxide gas present in a process environment and are described in United Kingdom patent application number 0308939.8 and GB 2,348, 006A, GB 2,119,933A respectively. Such sensors are generally formed from an electrochemical cell comprising a measurement electrode, a reference electrode and a solid state electrolyte of a suitable ionic conductor disposed between and bridging said electrodes.

For example, the gas monitor of GB 2,348.006A comprises a detection electrode containing a silver salt having an anion, which corresponds to the gas to be detected, a silver ion conducting solid state electrolyte and a reference silver electrode. The gas monitor can be used to detect gases such as carbon dioxide, sulphur dioxide, sulphur trioxide, nitrogen oxides and halogens through the suitable choice of the appropriate anion.

For the oxygen sensors of United Kingdom patent application number 0308939.8, the solid state electrolyte conducts oxygen anions and the reference electrode is generally coated or formed from a catalyst that is able to catalyse the dissociative adsorption of oxygen and is positioned within a reference environment, in which the concentration of oxygen adjacent the reference electrode remains constant.

BRIEF SUMMARY OF THE INVENTION

Solid state oxygen anion conductors (solid state electrolytes) are generally formed from doped metal oxides such as gadolinium doped ceria or yttria stabilised zirconia (YSZ). At temperatures below the critical temperature for each electrolyte ($T_c$) the electrolyte material is non-conducting. At temperatures above $T_c$ the electrolyte becomes progressively more conductive.

Oxygen levels as determined by such sensors in any monitored environment is determined by the electrochemical potentials generated by the reduction of oxygen gas at both the measurement and reference electrodes. The steps associated with the overall reduction reactions at each electrode are set out below, the half-cell reaction at each electrode being defined by equations 1 and 2 below.

$$O_{2(gas)} \leftrightharpoons 2O_{(ads)} \quad \text{(Equation 1)}$$

$$O_{(ads)} + 2e^- \leftrightharpoons O^{2-} \quad \text{(Equation 2)}$$

The electrochemical potential generated at each electrode is determined by the Nernst equation:

$$E = E^\ominus + \frac{RT}{2F} \ln \frac{a(O_{ads})}{a(O^{2-})} \quad \text{Equation 3}$$

where

E is the electrochemical half-cell potential at the reference or measurement electrode respectively;

$E^\ominus$ is the standard electrochemical half cell potential of the cell at unit $O_{(ads)}$ activity R is the gas constant T is the temperature of the cell F is Faraday's constant $a(O_{ads})$ and $a(O^{2-})$ are the activities of the adsorbed oxygen at the electrode surface and reduced oxygen anion in the solid state ionic conductor respectively.

The activity of adsorbed oxygen at the electrode surface is directly proportional to the partial pressure of oxygen gas, $P_{O2}$, in the environment adjacent the electrode as defined by equation 4 below:

$$a(O_{ads}) = KP_{O_2}^{1/2} \quad \text{Equation 4}$$

Since $a(O^{2-})$ is unity, by definition, and the activity of the adsorbed oxygen at the electrode surface is proportional to the partial pressure of the oxygen in the environment adjacent the electrode surface (equation 4), the half cell potential can be written in terms of the partial pressure of oxygen in the particular environment adjacent the measurement or reference electrode respectively $$E = E^\ominus + \frac{RT}{4F} \ln p_{O_2} \quad \text{Equation 5}$$

The potential difference V generated across the cell is defined in terms of the difference in the half-cell potentials between the reference and measurement electrodes in accordance with equation 6.

$$V = E_{(R)} - E_{(M)} = \frac{RT}{4F} \ln \left( \frac{P_{O2(R)}}{P_{O2(M)}} \right) \quad \text{Equation 6}$$

where

V is the potential difference across the cell $E_{(R)}$ and $E_{(M)}$ are the electrochemical potentials at the reference and measurement electrodes respectively;

R, T and F are as defined above; and $P_{O2(R)}$ and $P_{O2(M)}$ are the partial pressures of oxygen at the reference and measurement electrodes respectively.

Note that if both the reference and measurement electrodes are exposed to the same oxygen partial pressure e.g. atmospheric levels of oxygen, the potential difference across the cell is zero. In process environments such as the oxygen deficient environments encountered in the manufacture of semiconductor products the partial pressure of oxygen adjacent the measurement electrode is considerably less than that adjacent the reference electrode. Since the electrochemical potential at each electrode is governed by the Nernst equation, as the partial pressure of oxygen at the measurement electrode decreases, the electrochemical potential at the measurement electrode changes, which results in the formation of a potential difference across the cell at temperatures above the critical temperature. The potential difference across the cell is determined by the ratio of the partial pressure of oxygen at the reference and measurement electrodes in accordance with equation 6 above. The oxygen sensor can therefore provide a user with an indication of the total amount of oxygen present in a monitored environment simply from determining the potential difference across the cell.

However, there is a need for a similar simple, low cost, semi-quantitative sensor, which has a low sensitivity to unreactive organic compounds but can be used at the point of use to analyse the process environment. In at least its preferred embodiment, the present invention seeks to address that need.

A first aspect of the present invention provides an organic contaminant molecule sensor for use in a low oxygen concentration monitored environment, the sensor comprising an electrochemical cell comprising a solid state oxygen anion conductor in which oxygen anion conduction occurs at or above a critical temperature $T_c$, a measurement electrode formed on a first surface of the conductor for exposure to the monitored environment, the measurement electrode comprising material for catalysing the dissociative adsorption of the organic contaminant molecule, and a reference electrode formed on a second surface of the conductor for exposure to a reference environment, the reference electrode comprising material for catalysing the dissociation of oxygen to oxygen anions; means for controlling and monitoring the temperature of the cell; and means for controlling the electrical current flowing between the reference and measurement electrodes, whereby at temperatures below $T_c$, organic contaminant molecules are adsorbed onto and dissociated at the surface of the measurement electrode leading to the build up of carbonaceous deposits at the surface thereof, and at temperatures above $T_c$, an electrical current is passed between the reference and measurement electrode thereby to control the number of oxygen anions passing from the reference electrode to the measurement electrode to oxidise the carbonaceous deposits formed at the surface thereof and the formation of carbon dioxide.

The reference environment may, for example, be a gaseous source of oxygen at constant pressure (such as atmospheric air) or a solid-state source of oxygen, typically a metal I metal oxide couple such as $Cu/Cu_2O$ and $Pd/PdO$ or a metal oxide/metal oxide couple such as $Cu_2O/CuO$.

Suitable electrode materials include metals selected from the group comprising rhenium, osmium, iridium, ruthenium, rhodium, platinum and palladium and alloys thereof. Alloys of the aforementioned materials with silver, gold and copper may also be used.

Sensing, reference and optionally counter electrodes can be applied to a thimble of an oxygen anion conductor solid state electrolyte such as yttria stabilised zirconia either in the form of an ink or a paint or using techniques such as sputtering.

The reference electrode is suitably formed from a material that is able to catalyse the dissociation of oxygen in the reference environment, for example platinum. The reference environment can be derived from a gaseous or solid-state source of oxygen. Solid-state sources of oxygen typically comprise of a metal/metal oxide couple such as $Cu/Cu_2O$ and $Pd/PdO$ or a metal oxide/metal oxide couple such as $Cu_2O/CuO$. Suitable oxygen anion conductors include gadolinium doped ceria and yttria stabilised zirconia.

It will further be appreciated that the sensor of the first aspect of the invention can be used in a method for monitoring the level of trace organic contaminants in process environments. A third aspect of the invention thus provides a method of monitoring the levels of trace organic contaminants in a monitored process environment, the method comprising the steps of providing an electrochemical sensor comprising a solid state oxygen anion conductor in which oxygen anion conduction occurs at or above a critical temperature $T_c$, a measurement electrode formed on a first surface of the conductor for exposure to the monitored environment, the measurement electrode comprising material for catalysing the dissociative adsorption of the organic contaminant molecule, and a reference electrode formed on a second surface of the conductor for exposure to a reference environment, the reference electrode comprising material for catalysing the dissociation of oxygen to oxygen anions; exposing the measurement electrode at a sensor temperature $T_{ads}$ to the monitored environment for a time $t_{ads}$ to cause one or more organic contaminant species to be adsorbed onto and dehydrogenate at the surface of the measurement electrode thereby leading to the build up of a carbonaceous deposit at the surface thereof; raising the temperature of the sensor to a value $T_{tit}$ above the critical temperature $T_c$ of the solid state oxygen anion conductor and passing a current $I_p$ between the reference electrode and the measurement electrode for a time $t_p$ taken for the potential difference across the sensor to reach a constant value determined by the equilibrium between the flux of oxygen anions arriving at the electrode surface and the rate of desorption of oxygen gas from the electrode surface; and determining from the total charge ($I_p t_p$) passed through the sensor at temperature $T_{tit}$ the amount of carbonaceous deposit present at the surface of the measurement electrode and therefore the concentration of organic contaminant species present in the process environment.

BRIEF DESCRIPTION OF THE DRAWINGS

Preferred features of the present invention will now be described, by way of example only, with reference to the accompanying drawings, in which.

DETAILED DESCRIPTION OF THE INVENTION

Figure 1:
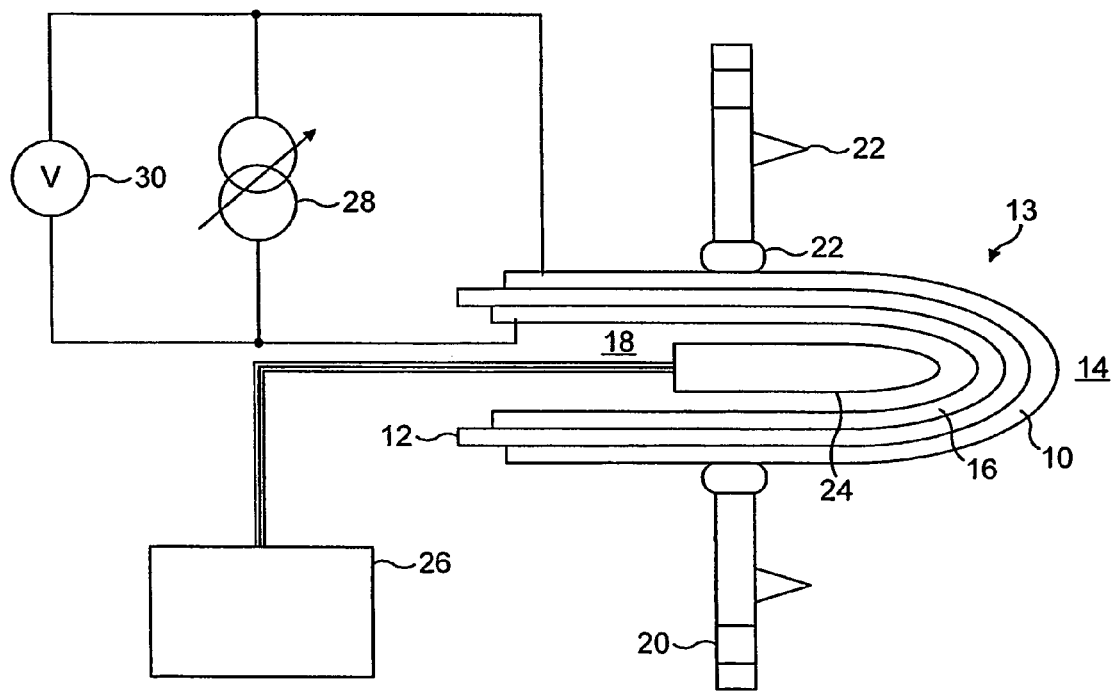
FIG. 1 illustrates a first embodiment of an electrochemical sensor.

The electrochemical sensor of FIG. 1 comprises a measurement electrode 10 deposited on one side of a solid state electrolyte 12 comprising an yttrium stabilised zirconium oxygen anion conductor tube. The measurement electrode may be deposited using a technique such as vacuum sputtering or applying any suitable commercially available "ink" to the surface. In the event that the measurement electrode 10 is formed on the surface of the electrolyte 12 using ink, the whole assembly must be fired in a suitable atmosphere determined by the nature of the ink. In the preferred embodiment, the measurement electrode 10 is formed from platinum. Alternatively, the measurement electrode 10 may be formed from any other material that is able to catalyse the dehydrogenation of a hydrocarbon contaminant such as propylene to carbonaceous material at its surface. In use the measurement electrode 10 is placed in contact with a monitored environment 14.

A reference electrode 16 is formed on the opposite surface of the electrolyte 12 to the measurement electrode 10 using similar techniques to those described above for measurement electrode 10. In the preferred embodiment, the reference electrode 16 is formed from platinum. Alternatively, the reference electrode 16 may be formed from any other material that is able to catalyse the dissociation of oxygen to oxygen anions. In use, the reference electrode 16 is placed in contact with a reference environment 18, which, in this embodiment, is a gaseous source of oxygen at constant pressure such as atmospheric air. Typically atmospheric air is used as a gaseous reference source of oxygen although other gas compositions can be used. The electrodes 10, 16 and the electrolyte 12 together form an electrochemical cell 13.

The sensor is mounted in the environment to be monitored using a mounting flange 20, and the measurement electrode 10 is typically isolated from the reference electrode 16 through the use of gas tight seals 22. In this way it is possible to separate the monitored environment 14 from the reference electrode 16 and the reference environment 18.

A radiative heater may be used to control the temperature of the cell. Such heaters include heating filaments, wound around the solid state electrolyte. An electric light bulb can also be used. A thermocouple may be used to monitor the temperature of the cell.

The sensor of FIG. 1 is provided with a heater and thermocouple assembly 24 for heating the sensor and for providing an indication of the temperature of the sensor. The heater and/or thermocouple may be, as illustrated, a self contained cartridge assembly, or may be bonded to the electrolyte prior to the formation of the electrodes; sputtered onto the electrolyte subsequent to the formation of the electrodes or wound round the electrolyte prior to or subsequent to the isolation of the sensing electrodes from the reference and counter electrodes. The temperature of the sensor is controlled by a suitable control device 26.

A constant current source 28 is also provided to control the current flowing from the reference electrode 16 to the measurement electrode 10. A voltammeter 30 is also provided to measure the potential difference across the cell.

Currents of between 100 nA and 100 pA may be used for driving oxygen anions between the reference and measurement electrodes. Currents outside this range can be used depending upon the circumstances. The magnitude of the current used to drive the oxygen anions between the reference and measurement electrodes depends upon the surface area of the electrode and the amount of cracked hydrocarbon deposited at the surface thereof. Larger currents will generally be required for electrodes having a greater surface area or a large amount of cracked hydrocarbon deposited on the surface thereof. The sensor is preferably used in conjunction with a device for measuring the potential produced across the cell.

In use, the sensor continuously cycles between an adsorption mode and an oxygen titration mode:

In the adsorption mode, the sensor is held at a constant temperature, $T_{ads}$, which is below the critical temperature, $T_c$, for oxygen anion conduction within the solid state electrolyte. The $T_c$ for YSZ, for example, is in the range 300° C. $T_{ads}$ and the sensing electrode material are chosen such that the catalytic properties of the sensing electrode, at $T_{ads}$, cause adsorbed organic material to de-hydrogenate/crack leading to the build up of carbonaceous deposits on the surface. For a platinum electrode, for example, $T_{ads}$ is in the range 20 to 80° C. In the ideal case complete de-hydrogenation/cracking will occur leaving a surface layer of adsorbed carbon.

The sensor is held at temperature, $T_{ads}$, for a time, $t_{ads}$, during which adsorption of the organic contaminants occurs. The length of time, $t_{ads}$, is suitably between 10 and 105 seconds and is preferably of the order of 102-103 seconds. Greater sensitivities can be achieved using longer adsorption times. It is, however, desirable that saturation of the measurement electrode during the adsorption phase is avoided as this will change the sticking/reaction probability of the surface, typically surface coverages of <0.5 monolayers are desirable. In the event that saturation of the electrode occurs this can be overcome by burning the carbonaceous deposit off of the surface of the measurement electrode and re-adsorbing for a shorter period of time.

In the event that incomplete cracking of the hydrocarbon contaminant occurs during the adsorption phase, complete cracking can be achieved by raising the temperature of the sensor to a temperature intermediate that of the adsorption temperature, $T_{ads}$, and the titration temperature, $T_{tit}$, and optionally applying a potential $V_i$ across the sensor, under which conditions complete cracking of the adsorbed hydrocarbon occurs. In some applications, $V_i$ may be zero. The sensor is held at the intermediate temperature for a period of time sufficient to allow complete conversion of any uncracked hydrocarbon contaminant to a carbonaceous deposit on the surface of the measurement electrode.

In use, the sensor of FIG. 1 is cycled between an adsorption phase and a titration phase. In the adsorption phase, the measurement electrode 10 is exposed to an environment to be monitored, including any organic contaminants. As discussed above, the sensor is held at a temperature $T_{ads}$ for a time $t_{ads}$ during which any organic contaminants are adsorbed onto and dehydrogenated at the surface of the measurement electrode 10, resulting in the formation of carbonaceous deposits thereat. The sensor then enters the titration phase. The temperature of the sensor is raised to a temperature $T_{tit}$ above the critical temperature $T_c$ of the electrolyte at which the electrolyte becomes conducting. Once at temperature $T_{tit}$ a known current $I_p$ is passed between the reference electrode 16 and the measurement electrode 10 thereby to force oxygen anions to pass from the reference electrode to the measurement electrode where they are oxidised and react with the carbonaceous deposits formed at the surface of the measurement electrode during the adsorption phase to form carbon dioxide.

In the oxygen titration mode, the sensor temperature is rapidly raised from either the adsorption temperature, $T_{ads}$, or the intermediate temperature to a fixed absolute temperature, $T_{tit}$, which is above $T_o$. During this temperature ramp de-hydrogenated organic material will remain on the surface. Once at $T_{tit}$, a small current $I_p$ is forced to pass through the electrochemical cell, pumping oxygen to the sensing electrode surface, as per equation 7. Currents of the order of 100 nanoamps to 100 micro-amps are suitably used. The oxygen progressively combusts the carbonaceous residue on the sensing electrode in accordance with equation 8.

$2O^{2-} \rightarrow 2O_{(ads)} + 4e^-$  Equation 7

$C_{(ads)} + 2O_{(ads)} \rightarrow CO_2$  Equation 8

The potential of the sensing electrode, relative to the reference electrode, will tend to the equilibrium thermodynamic value predicted by the Nernst equation 3, as the titration reaction proceeds. When the equilibrium thermodynamic voltage $V_o$ is reached the oxygen titration reaction is complete. The total amount of charge that has flowed through the cell during the titration reaction is directly proportional to the amount of oxygen reacted. For the ideal case the amount of carbon accumulated during the adsorption phase will be ¼ of the total charge, as per equations 7 and 8. The amount of carbon can be determined from the time taken in the adsorption phase and the surface area of the sensing electrode.

The total amount of carbonaceous deposit formed at the surface of the measurement electrode can be determined by measuring the total amount of oxygen transported to the measurement electrode by the application of current $I_p$ (which is required to oxidise all of the carbonaceous deposits) over the time $t_p$ taken for the potential difference across the cell to return from $V_{tit}$ to $V_o$. Since the transport of each oxygen anion to the surface of the measurement electrode requires the passage of two units of charge, the total quantity of oxygen atoms transported to the surface of the electrode is determined by the term:

$I_p t_p / 2$  Equation 9

Since each atom of carbon deposited at the surface of the electrode requires two oxygen atoms for complete combustion, the total amount of carbon atoms oxidised during the titration phase and hence deposited at the electrode during the adsorption phase is:

$I_p t_p / 4$  Equation 10

During the titration phase the potential difference across the cell is monitored, together with the time taken for the potential difference to reach a constant value, $V_o$, characterised by the current $I_p$. In the absence of organic contaminants, at temperature $T_{tit}$ and constant electrical current $I_p$, the potential difference across the cell, $V_o$, is constant and is determined by the equilibrium between the flux of oxygen anions ($O^{2-}$) arriving at the electrode surface and the rate of desorption of oxygen gas ($O_{2(g)}$) from the electrode surface according to equations 1 and 2 above.

However, when carbonaceous deposits are present on the electrode surface they are oxidised (combusted) to carbon dioxide by the flux of oxygen anions arriving at the electrode surface. This has the effect of reducing the equilibrium concentration of oxygen anions ($O^{2-}$) at the surface, which means that, in accordance with equation 3 above, the potential across the cell, $V_{tit}$, is increased relative to $V_o$. When the current $I_p$ is applied to the cell, oxygen anions are forced to flow from the reference electrode to the measurement electrode where they react with the carbonaceous deposits formed at the surface thereof during the adsorption phase, which results in the formation of carbon dioxide. As the carbonaceous deposits are transformed into carbon dioxide their concentration progressively decreases to zero at the surface of the measurement electrode and the concentration of oxygen at the surface of the measurement electrode will increase to the constant equilibrium value determined by the flux of oxygen anions to the electrode. The potential difference across the cell then returns to the constant value, $V_o$, and provides an indication that all the carbonaceous deposits on the surface of the electrodes have been removed.

The establishment of this constant potential indicates that sufficient oxygen has passed between the reference and measurement electrodes to cause complete oxidation of all of the carbonaceous deposits present at the surface of the measurement electrode 10 and therefore that the end point of the oxidative titration has been reached.

By measuring the time taken for all the carbonaceous deposits on the surface of the measurement electrode to be oxidised, it is possible to determine the amount of carbonaceous deposit formed at the surface thereof during the adsorption phase. Since the length of the adsorption phase is known, it is then possible to determine the amount of carbonaceous deposit formed on the surface of the electrode per unit time and from this the concentration of trace organic materials in the process environment.

It will be appreciated that by controlling the time over which adsorption of the organic contaminants can occur on the surface of the measurement electrode, the value of the current $I_p$ flowing between the reference and measurement electrodes at temperature $T_{tit}$ and the time $t_p$ taken for the potential difference across the cell to drop from $V_{tit}$ to $V_o$, it is possible to titrametrically monitor the levels of organic contaminants in the process environment in the parts per trillion (ppt) range or less. The sensor therefore provides a low cost alternative to the use of mass spectrometry and gas chromatography in the determination of low levels of organic impurities in process environments.

Although the sensor can be used with just two electrodes (the reference and measurement electrode) only, it is preferred to use an electrode arrangement comprising a counter electrode in addition to the measurement and reference electrodes as described above. The counter electrode is positioned adjacent to the reference electrode and in contact with the same reference environment as the reference electrode. In this preferred embodiment, the current $I_p$ flows between the counter electrode and the measurement electrode. The reference electrode therefore provides a constant reference environment from which the electrochemical potentials of both the measurement and counter electrodes and therefore the potential difference across the cell can be determined. The counter electrode is preferably formed from a material, such as platinum, which catalyses the dissociation of oxygen.

Figure 2:
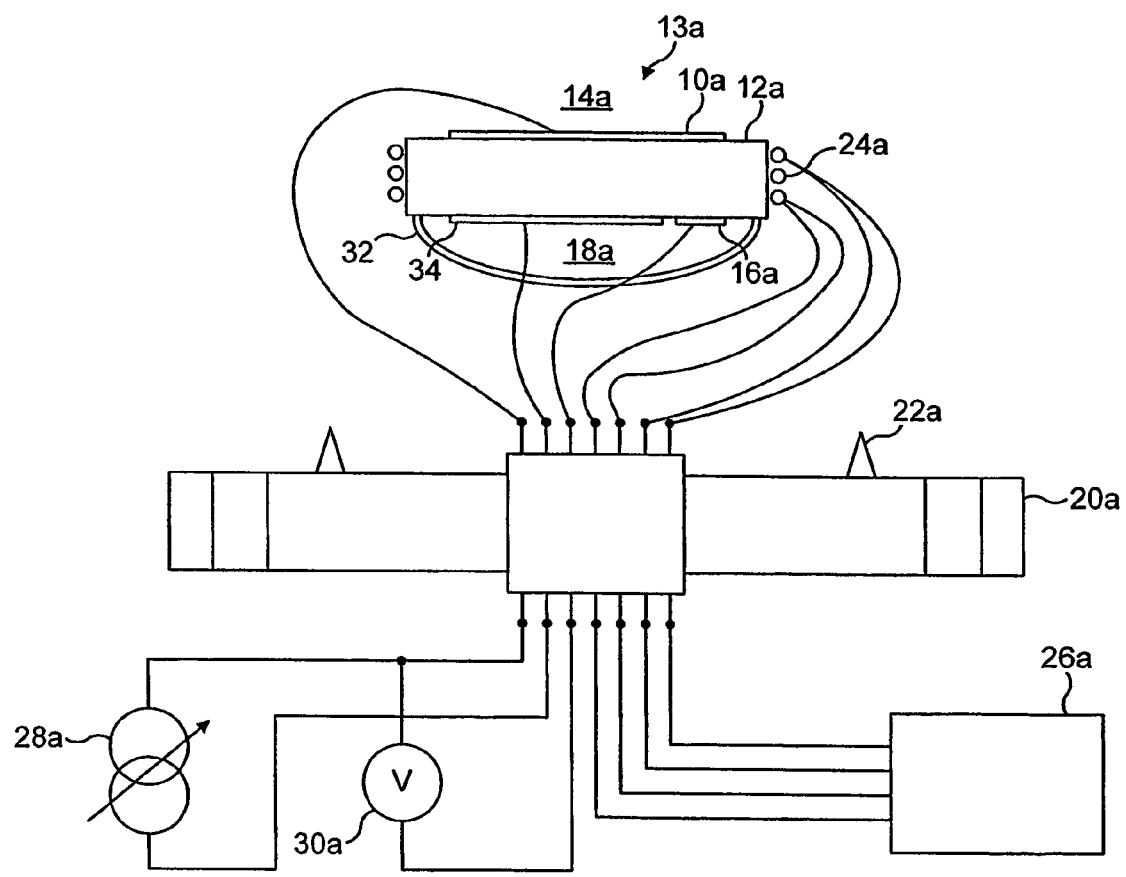
FIG. 2 illustrates a second embodiment of an electrochemical sensor.

FIG. 2 illustrates a second embodiment of a sensor, in which the reference numerals refer to the same elements as indicated above, except that the suffix "a" has been added to distinguish the two forms of sensor. In this embodiment, the reference environment is provided by a solid state reference material which is sealed from the sensing environment by sealing material 32, typically a glass material. This embodiment also includes an optional counter electrode 34.

In this embodiment the current generating means 28a passes the constant current between the counter electrode 34 and the measurement electrode 10a so as to minimize errors generated in the voltage measuring device 30a. The voltage measuring device 30a measures the voltage between the measurement electrode 10a and the reference electrode 16a.

Sensing, reference and optionally counter electrodes can be applied to a thimble of an oxygen anion conductor solid state electrolyte such as yttria stabilised zirconia either in the form of an ink or a paint or using techniques such as sputtering. The sensing electrode is isolated from the reference and optional counter electrode via the formation of a gas tight seal. The sensor is suitably supplied with heater means to control the temperature of the electrolyte and means to monitor the voltage between the sensing electrode and the reference and counter electrodes respectively.

The sensor is also easy to use and can be used at the point of use as well as the point of entry to provide accurate information about the process environments at all stages of the semiconductor fabrication process. The sensor is easily and readily manufactured using techniques known to a person skilled in the art.

The total level of contaminants measured by the sensor can provide a semi-quantitative indication of the level of harmful organic contaminants present in the process environment. The non-contaminating light organic molecules present in the process environment do not stick to the surface of the measurement electrode and are not therefore measured. It is only the harmful organic contaminants, which have a high reaction probability with the electrode surface (and therefore with other surfaces encountered in the fabrication process) that undergo dissociation and are therefore subsequently oxidised at the measurement electrode surface that are detected and therefore monitored by the measurement electrode.

Careful choice of the material applied to the measurement electrode or the material from which it is formed will cause some of the harmful organic contaminants to adsorb onto the surface of the measurement electrode in preference to others. Preferably the measurement electrode is formed from material whose uptake of organic material proceeds with a sticking probability of or about unity. In addition, the organic material is preferably efficiently adsorbed and cracked by the electrode material. Furthermore, the measurement electrode is suitably able to catalyse the dehydrogenation and cracking of organic contaminants.

Solid-state sources of oxygen typically comprise of a metal/metal oxide couple such as $Cu/Cu_2O$ and $Pd/PdO$ or a metal oxide/metal oxide couple such as $Cu_2O/CuO$. The particular solid-state reference materials chosen will depend on the operating environment of the sensor and in particular the titration temperature $T_{tit}$. The solid state electrolyte comprising an oxygen anion conductor is suitably formed from a material that exhibits oxygen anion conduction at temperatures above 300° C.

The dimensions of the top and bottom surfaces of the sensor are typically of the order of a few square centimeters or less. The electrodes formed or deposited on each of the surfaces are therefore dimensioned accordingly. The sensing and counter electrodes are each typically of the order of 1 cm². The reference electrode is usually of a lesser dimension. The electrodes are typically from about 0.1 to about 50 um in thickness.

It will be appreciated that the sensor can be used to monitor the levels of trace organic contaminants in process environments, and so a second aspect of the invention provides the use of a sensor as aforementioned to monitor levels of trace organic contaminants in process environments.

Figure 3:
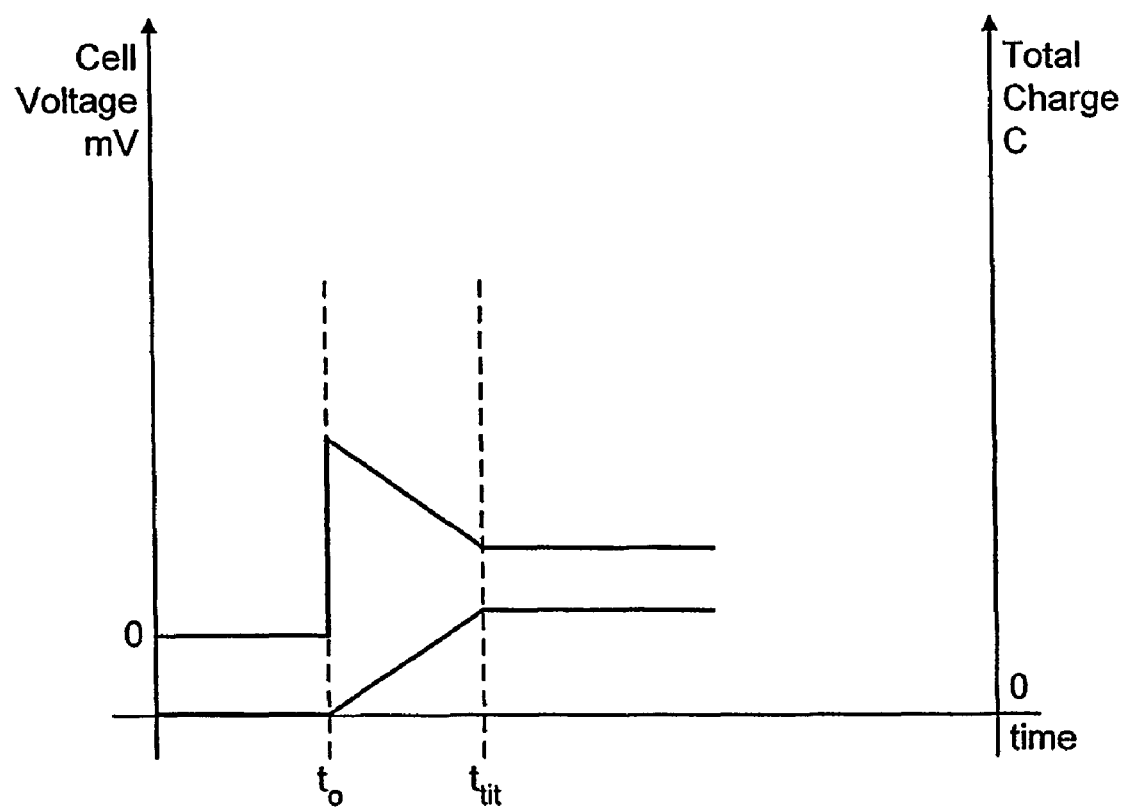
FIG. 3 illustrates the relationship between the voltage across the cell and the total charge passed therethrough during the titration time $t_{tit}$.

FIG. 3 illustrates the change in both the total charge passed through the cell and the measured potential difference across the cell during the passage of such charge over titration time $t_{tit}$. The lower curve represents total charge passed and the upper curve represents potential difference across the cell. It can be seen that as the total charge increases to a maximum value the potential difference across the cell decreases from a maximum value to a minimum constant value. The time taken for the potential difference across the cell to change from the maximum value determined upon application of the current $I_p$ to the cell to the minimum constant value is the time taken for oxidation of all the carbonaceous deposits from the surface of the measurement electrodes.

EXAMPLES

Example 1

Construction of the Sensor

Reference, and measurement electrodes, and optional counter electrode, were formed on a thimble/disc of the oxygen anion conducting electrolyte (commercially available from various suppliers) by sputtering under vacuum or using commercially available 'inks' and firing the assembly in a suitable atmosphere according to the procedure given by the ink manufacturer.

A gas tight seal (resistant to both vacuum and pressure) was formed around the oxygen anion conducting electrolyte to isolate the measurement electrode from the reference electrode and optional counter electrode using standard procedures. Depending upon how the sensor is to be heated the heater/thermocouple can be added at any appropriate stage during manufacture.

Example 2

Determination of the TOC Levels in a Process Gas

A sensor having a YSZ solid state electrolyte having a $T_c$ of 300° C. and a platinum measurement electrode with a surface area (A) of 1 cm², the electrode having a surface density, ρ, of $10^{15}$ atoms/cm², was exposed to a process gas containing propylene at a temperature of $T_{ads}$ for a time $t_{ads}$ of $10^3$ seconds. The average sticking probability, S, for organic contaminants on the sensing electrode is 0.1. The temperature of the sensor was raised to $T_{tit}$ and a current $I_p$ of $2\times10^{-6}$ A was passed between the reference and measurement electrode. During the passage of the current the potential difference across the cell dropped to a constant value of 350 mV over a period $t_{tit}$ of 100 seconds. The total charge passed between the reference and measurement electrode was thus $2.10^{-3}$ Coulombs, which corresponds to the formation of 0.3 monolayers of carbonaceous deposit in accordance with equation 11.

$$M = \frac{I_{tit} t_{tit}}{4e} \frac{1}{A\rho} \quad \text{Equation 11}$$

The total equivalent partial pressure (mbar) of the organic contaminant (expressed as equivalents of carbon atoms) is calculated as $1.0\times10^{-8}$ mbar or 1.0 ppt using equations 12, 13 below.

$$P_{TOC} = \frac{M}{St_{ads}} \times 3.4 10^{-6} \quad \text{Equation 12}$$

$$TOC_{(ppt)} = P_{TOC} \times 10^{-9} \quad \text{Equation 13}$$

I claim:

1. An organic contaminant molecule sensor for use in a process environment having a low oxygen concentration comprising:
   an electrochemical cell comprising:
      a solid state oxygen anion conductor in which oxygen anion conduction occurs at or above a critical temperature;
      a measurement electrode formed on a first surface of the anion conductor for exposure to the monitored environment, the measurement electrode comprising a material for catalyzing the dehydrogenation of an organic contaminant molecule wherein at temperatures below the critical temperature, organic contaminant molecules are adsorbed onto and dehydrogenated at the surface of the material of the measurement electrode to form a carbonaceous deposit on the surface of the material of the measurement electrode; and
      a reference electrode formed on a second surface of the anion conductor for exposure to a reference environment, the reference electrode comprising a material for catalyzing the dissociation of oxygen to oxygen anions;
   a heater for controlling the temperature of the electrochemical cell in a manner that the heater sets a temperature of the solid state oxygen anion conductor below the critical temperature during an adsorption phase, and at or above the critical temperature during a titration phase; and
   a current source for controlling the electrical current between the reference electrode and the measurement electrode wherein at temperatures above the critical temperature, an electrical current is passed between the reference electrode and the measurement electrode to control the number of oxygen anions passing from the reference electrode to the measurement electrode to oxidize the carbonaceous deposit.

2. The sensor according to claim 1 wherein the measurement electrode comprises a metal selected from the group of metals consisting of rhenium, osmium, iridium, ruthenium, rhodium, platinum and palladium and alloys thereof.

3. The sensor according to claim 2 wherein the alloys include an element selected from the group of elements consisting of silver, gold and copper.

4. The sensor according to claim 3 wherein the reference electrode comprises a metal capable of dissociating oxygen.

5. The sensor according to claim 1 wherein the solid state oxygen anion conductor is selected from the group of conductors consisting of gadolinium doped ceria and yttria stabilized zirconia.

6. The sensor according to claim 1 comprising a counter electrode positioned adjacent to the reference electrode.

7. The sensor according to claim 6 wherein the counter electrode comprises a metal capable of dissociating oxygen.

8. The sensor according to claim 1 comprising a reference environment having a gaseous source of oxygen at atmospheric pressure.

9. The sensor according to claim 1 wherein the reference environment comprises a solid state source of oxygen.

10. The sensor according to claim 9 wherein the solid state source of oxygen comprises a metal/metal oxide compound.

11. The sensor according to claim 1 wherein the heater further includes a thermocouple assembly.

12. The sensor according claim 1 further including means for measuring a potential across the sensor.

13. The sensor according to claim 12 wherein the sensor monitors the levels of trace organic contaminants in a low oxygen concentration monitored process environment.

14. The sensor according claim 11 further including a device for measuring a potential across the sensor.

15. The sensor according to claim 14 wherein the sensor monitors the levels of trace organic contaminants in a low oxygen concentration monitored process environment.

16. The sensor according to claim 11 wherein the measurement electrode comprises a metal selected from the group of metals consisting of rhenium, osmium, iridium, ruthenium, rhodium, platinum and palladium and alloys thereof.

17. The sensor according to claim 16 wherein the alloys include an element selected from the group of elements consisting of silver, gold and copper.

18. The sensor according to claim 6 wherein the heater further includes a thermocouple assembly.

19. The sensor according claim 18 further including means for measuring a potential across the sensor.

20. The sensor according to claim 19 wherein the sensor monitors the levels of trace organic contaminants in a low oxygen concentration monitored process environment.

21. The sensor according to claim 20 wherein the reference electrode comprises platinum, palladium or other metal capable of dissociating oxygen.

22. The sensor according to claim 6 wherein the measurement electrode comprises a metal selected from the group of metals consisting of rhenium, osmium, iridium, ruthenium, rhodium, platinum and palladium and alloys thereof.

23. The sensor according to claim 22 wherein the alloys include an element selected from the group of elements consisting of silver, gold and copper.

24. The sensor according to claim 12 wherein the measurement electrode comprises a metal selected from the group of metals consisting of rhenium, osmium, iridium, ruthenium, rhodium, platinum and palladium and alloys thereof.

25. The sensor according to claim 24 wherein the alloys include an element selected from the group of elements consisting of silver, gold and copper.

26. The sensor according to claim 25 wherein the reference electrode comprises a catalyst for the dissociation of oxygen.

27. The sensor according to claim 26 wherein the reference electrode comprises a metal capable of dissociating oxygen.

28. The sensor according to claim 12 wherein the solid state oxygen anion conductor is selected from the group of conductors consisting of gadolinium doped ceria and yttria stabilized zirconia.

29. The sensor according to claim 12 comprising a reference environment having a gaseous source of oxygen at atmospheric pressure.

30. The sensor according to claim 12 wherein the reference environment comprises a solid state source of oxygen.

31. The sensor according to claim 30 wherein the solid state source of oxygen comprises a metal/metal oxide compound.

32. The sensor according to claim 4 wherein the metal capable of dissociating oxygen is selected from the group of metals consisting of platinum and palladium.

33. The sensor according to claim 7 wherein the metal capable of dissociating oxygen is selected from the group of metals consisting of platinum and palladium.

34. A sensor according to claim 9 wherein the solid state source comprises a metal oxide/metal oxide compound.

35. The sensor according to claim 27 wherein the metal capable of dissociating oxygen is selected from the group of metals consisting of palladium and platinum.

36. The sensor according to claim 30 wherein the solid state source of oxygen comprises a metal oxide/metal oxide compound.

* * * * *